(12) United States Patent
Lee et al.

(10) Patent No.: US 7,047,793 B2
(45) Date of Patent: May 23, 2006

(54) SENSITIVE SUBSTANCE AND SURFACE ACOUSTIC WAVE GAS SENSOR USING THE SAME

(75) Inventors: Kun-Hyung Lee, Gyeonggi-do (KR); Jung-Sung Hwang, Gyeonggi-do (KR); Seung-Yeon Cho, Gangwon-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 218 days.

(21) Appl. No.: 10/728,004

(22) Filed: Dec. 3, 2003

(65) Prior Publication Data

US 2004/0107765 A1    Jun. 10, 2004

(30) Foreign Application Priority Data

Dec. 9, 2002   (KR) ...................... 10-2002-0077689

(51) Int. Cl.
*G01N 29/02* (2006.01)
(52) U.S. Cl. .................................... 73/24.06
(58) Field of Classification Search ............ 73/24.06, 73/31.05, 579, 590
See application file for complete search history.

(56) References Cited

U.S. PATENT DOCUMENTS 3,938,263 A * 2/1976 Tate ........................ 434/409
5,837,446 A * 11/1998 Cozzette et al. ............... 435/6
6,004,494 A   12/1999 Debe

FOREIGN PATENT DOCUMENTS

JP          9-210975          8/1997

OTHER PUBLICATIONS

English language abstract and machine translation of Japanese Patent Publication 09-210975 of Aug. 15, 1997.*
English language abstract of Japanese Publication No. 09-210975.

* cited by examiner

*Primary Examiner*—Charles Garber
(74) *Attorney, Agent, or Firm*—Marger Johnson & McCollom, P.C.

(57) ABSTRACT

A surface acoustic wave gas sensor for detecting predetermined substances includes a piezoelectric substrate, an input transducer and an output transducer which is formed on the piezoelectric substrate, and a sensitive film which is formed between the input transducer and the output transducer and detects at least one of acetone, benzene, dichloroethane, ethanol, and toluene. The sensitive film includes mercaptoundecanoic acid and CMP composed of cellulose nitrate, dibutyl phthalate, compound of benzene and ethanol, ethyl acetate. The surface acoustic wave gas sensor can quickly detect even small amounts of these substances.

20 Claims, 3 Drawing Sheets

Fig. 2

LOD : mg/m³     S : HZ/(mg/m³)

| Thickness of Film (KHZ) | Acetone | | Ethanol | | Benzene | | Toluene | | Dichloroethane | |
|---|---|---|---|---|---|---|---|---|---|---|
| | LOD | S(10⁻³) | LOD | S(10⁻³) | LOD | S(10⁻³) | LOD | S(10⁻³) | LOD | S(10⁻³) |
| NC (80.4) | 130 | 61 | 26 | 266 | | | 75 | 106 | | |
| MDA + CMP(50.0) | 5 | 2154 | 1.7 | 6400 | 12 | 126 | 4 | 4800 | 350 | 57 |

Fig. 3

|  |  | Acetone | Ethanol | Benzene | Toluene | Dichloroethane |
|---|---|---|---|---|---|---|
| NC | | 104 | 21 | | 60 | |
| MDA + CMP | | 2.5 | 0.9 | 3.6 | 2.0 | 180 |
| DOC1 | A | | 13 | | | |
| | B | | | 92 | | |
| DOC2 | C | | | | 32 | |
| | D | | | | | 70 |

SENSITIVE SUBSTANCE AND SURFACE ACOUSTIC WAVE GAS SENSOR USING THE SAME

CROSS REFERENCE TO RELATED APPLICATIONS

This application claims priority from Korean Patent Application No. 2002-77689, filed on Dec. 9, 2002, the contents of which are incorporated herein by reference in their entirety.

FIELD OF THE INVENTION

The present invention relates to a gas sensor for detecting predetermined substances in a semiconductor fabricating apparatus and, more particularly, to a sensitive substance which readily absorbs acetone, ethanol, benzene, toluene or dichloroethane, and to a surface acoustic wave gas sensor using the same.

BACKGROUND OF THE INVENTION

In semiconductor fabricating lines, keeping a high level of cleanliness is necessary in order to maintain clean rooms or process chambers. Accordingly, it is very important to quickly detect even small amounts of airborne molecular contaminants. A variety of monitoring systems have been proposed for monitoring airborne molecular contaminants (AMCs), such as acetone, ethanol, benzene, toluene or dichloroethane, in a semiconductor fabricating apparatus. Unfortunately, these monitoring systems are high-priced and require the passage of a considerable amount of time for analyzing the AMCs which are present.

A typical apparatus for detecting the presence of undesirable substances is a surface acoustic wave gas sensor. The surface acoustic wave gas sensor includes a piezoelectric substrate, an input transducer, an output transducer, and a sensitive film. An electrical signal applied to the input transducer is converted into a wave by the piezoelectric substrate. The signal is transmitted to the output transducer through the piezoelectric substrate acting as a transmission medium. The wave reaching the output transducer is converted into an electrical signal by the piezoelectric effect. When a substance to be detected is absorbed in the sensitive film, the frequency of the wave is fluctuated. Depending on the fluctuated frequency of the wave, it is possible to determine whether there is an undesirable substance present, as well as its concentration.

According to the substances to be detected, the surface acoustic wave gas sensor uses a sensitive film coated with a sensitive substance which can readily absorb an undesirable substance to be detected. The sensitive film must have a high sensitivity so as to be responsive to the presence of the substance, i.e., exhibit a low detection limit. Further, the sensitive film must retain its high sensitivity property relative to the gas to be detected, and it must detect the gas as soon as possible.

Presently, there is no substance which is sensitive to a material such as acetone. Although there are sensitive substances which are sensitive to ethanol, benzene, toluene, and dichloroethane, their sensitivities are low. Therefore, it takes a considerably long time to detect the presence and the amount of these substances.

SUMMARY OF THE INVENTION

The foregoing problems are addressed by the present invention and will be understood by reading and studying the following specification. The invention provides a sensitive material having a high sensitivity relative to acetone, ethanol, benzene, toluene, and dichloroethane and a surface acoustic wave gas sensor using the same.

According to an aspect of the present invention, the sensitive film is used to detect at least one of acetone, benzene, ethanol, toluene, and dichloroethane. CMP and MDA (mercaptoundecanoic acid) dissolved in acetone are coated on the piezoelectric substrate to form the sensitive film. The CMP is composed of cellulose nitrate, dibutyl phthalate, compound of benzene and ethanol, and ethyl acetate.

According to another aspect of the present invention, the sensitive film is used to detect at least one of acetone, ethanol, and toluene. The sensitive film is formed by coating cellulose nitrate dissolved acetone on the piezoelectric substrate.

BRIEF DESCRIPTION OF THE DRAWINGS

FIG. 2 is a table showing the limits of detection and sensitivity relative to a gas in case that cellulose nitrate dissolved in acetone is used as a sensitive substance and in case where CMP and MDA dissolved in acetone are used as a sensitive substance.

FIG. 3 is a table comparatively showing the limits of detection described in FIG. 2 and the best limits of detection stated in conventional documents.

DESCRIPTION OF THE PREFERRED EMBODIMENT

Figure 1:
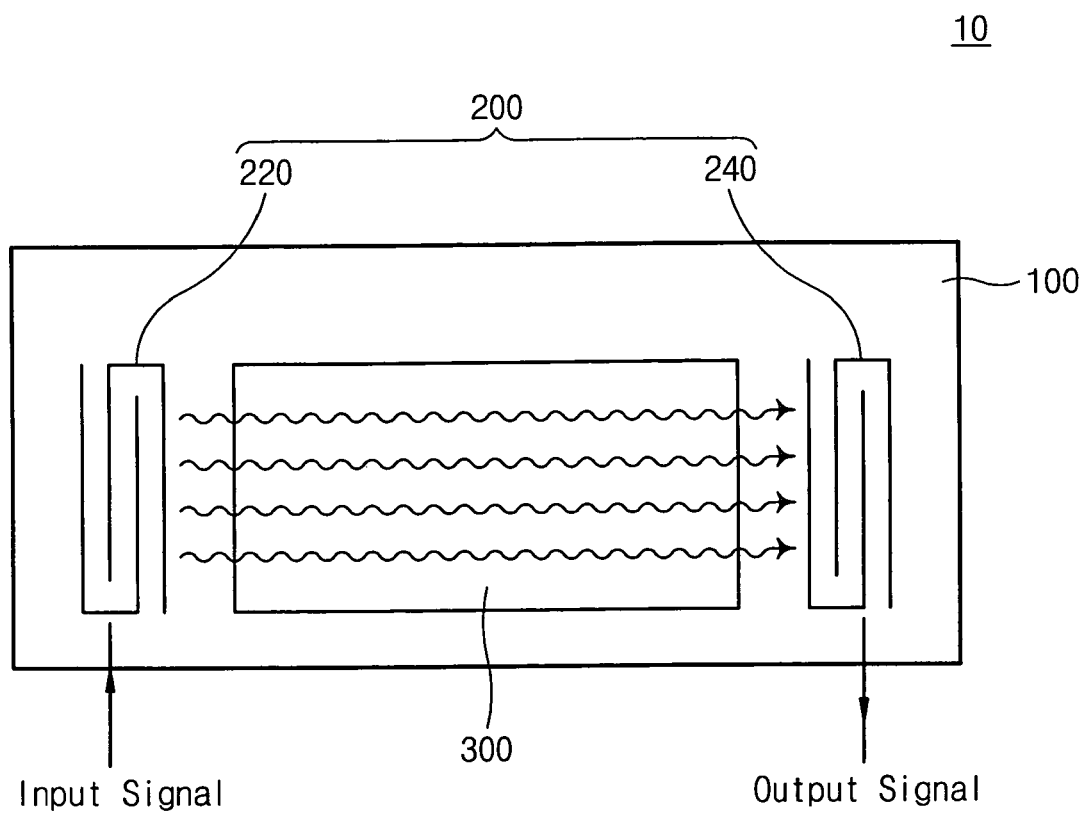
FIG. 1 is a cross-sectional view of a surface acoustic wave gas sensor according to an embodiment of the present invention.

Referring to FIG. 1, a surface acoustic wave gas sensor (hereinafter referred to as "SAW gas sensor") 10 includes a piezoelectric substrate 100, a transducer 200, and a sensitive film 300.

The piezoelectric substrate 100 converts an electrical signal into a mechanical surface acoustic wave, and then converts the surface acoustic wave into an electrical signal. Typically, the piezoelectric substrate 100 is made of $LiTaO_3$, $LiNbO_3$, or the like.

The transducer 200 has an input inter digital transducer (hereinafter referred to as "input IDT") 220 and an output inter digital transducer (hereinafter referred to as "output IDT") 240. The input IDT 220 transmits an electrical signal to the piezoelectric substrate 100, and the output IDT 240 transmits a transduced electrical signal from the piezoelectric substrate 100 to the outside. The converter 200 is made of aluminum formed in a pattern on the piezoelectric substrate 100. The input IDT 220 is disposed at one side of the piezoelectric substrate 100, and the output IDT 240 is disposed at the other side thereof. The input IDT 220 and the output IDT 240 are comb-patterned and spaced apart from each other.

The sensitive film 300 is coated on a portion between the input IDT 220 and the output IDT 240. The sensitive film 300 is used to readily absorb predetermined undesirable gases existing in a clean room or in a predetermined chamber (not shown) for conducting a semiconductor process.

When an alternating current (AC) voltage is applied to the input IDT 220, an acoustic wave is generated at the piezoelectric substrate 100. The acoustic wave is then transmitted to the output IDT 240 through a surface of the piezoelectric substrate 100. When predetermined gases are absorbed on the sensitive film 300 formed on the piezoelectric substrate 100 to increase the mass thereof, the frequency of the acoustic wave is varied to confirm whether the predetermined gas is present.

Generally, the kinds of substances used as the sensitive film 300 are variable with kinds of gases to be detected. In order to enable the SAW gas sensor to detect substances such as acetone, ethanol, benzene, toluene, and dichloroethane, the sensitive film 300 is made of a substance readily absorbing these substances, which is a feature of the present invention.

In accordance with one embodiment, the sensitive film 300 is formed by coating cellulose nitrate dissolved in the acetone onto the piezoelectric substrate 100. Preferably, the amount of the cellulose nitrate dissolved in the acetone is from about 0.3 to about 3.0 weight %.

In accordance with another embodiment of this invention, the sensitive film 300 can also be formed by coating CMP (which will be explained later in detail) and MDA (mercaptoundecanoic acid) dissolved in acetone onto the piezoelectric substrate 200. Preferably, the amount of CMP dissolved in the acetone is from about 0.3 to about 3.0 weight %, and the amount of the MDA dissolved therein is from about 0.05 to 0.5 about weight %.

The CMP preferably comprises from about 5 to 25 weight % of cellulose nitrate, from about 25 to about 50 weight % of dibutyl phthalate, from about 1 to about 10 weight % of a benzene-ethanol mixture, and from about 40 to about 60 weight % of ethyl acetate. The dibutyl phthalate softens the sensitive film, and the ethyl acetate is used as a solvent. The benzene-ethanol mixture stabilizes the viscosity and is preferably comprised of about 75 weight % of benzene and about 25 weight % of ethanol.

FIG. 2 is a table showing the preferred level of detection and sensitivity relative to a gas in the case where cellulose nitrate dissolved in acetone is used as a sensitive substance, and in the case where CMP and MDA are dissolved in acetone are used as a sensitive substance. FIG. 3 is a table comparatively showing the preferred limits of detection described in FIG. 2, and the limits of detection set forth in conventional systems in which LOD and S represent limits of detection and sensitivity, respectively. They can be exchanged for the same thickness film. Frequencies are varied with the thickness of film. In the present invention, the unit of the film thickness is indicated as the frequency in the thickness.

The limit of detection (LOD) means the amount of a predetermined substance that must exist per unit volume in order to be detectable. The lower the LOD is, the better the detectability for a given predetermined substance. The sensitivity (S) means a sensitive degree for a predetermined substance. The lower the LOD, the higher the S for a given predetermined substance.

Referring to FIG. 2 and FIG. 3, in case where acetone is to be detected, there is conventionally no substance readily absorbing and detecting the acetone. However, in case where cellulose nitrate or CMP and MDA are used as a sensitive film, the acetone may be detected. Particularly, in case that the CMP and MDA are used as the sensitive film, the sensitivity for the acetone is high and the limits of detection is low. Accordingly, the detectability for acetone is very excellent.

In case where the substances to be detected are ethanol, benzene, toluene, and dichloroethane, ethanol has the lowest LOD at a substance "A" stated as "OV275" in the document 1 (DOC1), and benzene has the lowest LOD at a substance "B" stated as "OV25" in the DOC1. Further, toluene has the lowest LOD at a substance "C" stated as "polyvinylproli-done" in the document 2 (DOC2), and dichloroethane has the lowest LOD at a substance "D" stated as "OV210" in the DOC2. The DOC1 is "Characterization of Polymeric Surface Acoustic Wave Sensor Coating and Semiempirical Models of Sensor Response to Organic Vapors" published by Samuel J. Patrash and Edward T. Zellars. The DOC2 is "Correlation of Surface Acoustic Wave Device Coating Responses with Solubility Properties and Chemical Structure Using Pattern Recognition" published by David S. Ballantine, Susan L. Rose, and Hank Wohltjen.

The SAW gas sensor 10 using the MDA and CMP as the sensitive film 300 has the lower LOD than the lowest-LOD substances, stated in the DOC1 and DOC2, relative to ethanol, benzene, toluene, and dichloroethane. For this reason, the SAW gas sensor 10 has a very excellent detectability relative to these substances. Further, the SAW gas sensor 10 using the cellulose nitrate as the sensitive film 300 has a somewhat higher LOD than the lowest-LOD substances, stated in the DOC1 and DOC2, relative to ethanol and toluene. However, while the substances stated in the DOC1 and DOC2 have the lowest LOD relative to each of these substances, the SAW gas sensor 10 may detect all the substances and its LOD is slightly different from the lowest LOD. Accordingly, it can be seen that the SAW gas sensor 10 exhibits excellent detectability.

In the experimental results shown, the SAW sensor coated with the foregoing sensitive substance can rapidly detect ethanol, benzene, toluene, and dichloroethane, when a substance such as ethanol has a high concentration as well as a low concentration.

In the above-described embodiment, the SAW gas sensor 10 uses cellulose nitrate or a substance including CMP and MDA as the sensitive film 300. The sensitive film can also be applied to a bulk acoustic gas sensor as well as the SAW gas sensor. In the case of the bulk acoustic gas sensor, a vibration waveform is transferred through bulk gas, not on the gas surface. Therefore, the present invention encompasses the cases of cellulose nitrate dissolved in acetone, and CMP and MDA dissolved in acetone, such that the SAW gas sensor detects the presence of substances such as acetone, ethanol, toluene, and dichloroethane.

It is apparent that many modifications and variations of the present invention may be made without departing from the spirit and scope of the invention. It is understood that the invention is not confined to the particular construction and arrangement herein described but embraces such modified forms of it as come within the appended claims. The specific embodiments described are given by way of example only and the invention is limited only by the terms of the appended claims.

What is claimed is:

1. A sensitive substance used in an acoustic wave gas sensor, the sensitive substance being dissolved in a solvent so as to detect predetermined substances in the acoustic wave gas sensor, wherein the sensitive substance comprises cellulose nitrate, dibutyl phthalate, a mixture of benzene and ethanol, ethyl acetate, and mercaptoundecanoic acid.

2. The sensitive substance of claim 1, wherein the predetermined substances are at least one of acetone, ethanol, and toluene.

3. The sensitive substance of claim 1, wherein the amount of cellulose nitrate dissolved in the solvent is from about 0.3 to about 3.0 weight %.

4. A sensitive substance used in an acoustic wave gas sensor, the sensitive substance being dissolved in a solvent so as to detect predetermined substances in an acoustic wave gas sensor and being used as a sensitive film, wherein the sensitive substance comprises:
CMP comprised of cellulose nitrate, dibutyl phthalate, a mixture of benzene and ethanol, and ethyl acetate; and mercaptoundecanoic acid.

5. The sensitive substance of claim 4, wherein the predetermined substances are at least one of acetone, ethanol, and toluene.

6. The sensitive substance of claim 4, wherein the CMP comprises:
from about 5 to about 25 weight % of cellulose nitrate;
from about 25 to about 50 weight % dibutyl phthalate;
from about 1 to about 10 weight % of a benzene-ethanol mixture; and
from about 40 to about 60 weight % of ethyl acetate.

7. The sensitive substance of claim 6, wherein the amount of the CMP dissolved in the solvent is from about 0.3 to about 3.0 weight %, and the amount of the mercaptoundecanoic acid dissolved therein is from about 0.05 to about 0.5 weight %.

8. The sensitive substance of claim 7, wherein the CMP comprises a mixture of about 75 weight % benzene and about 25 weight % ethanol.

9. The sensitive substance of claim 4, wherein the amount of the CMP dissolved in the solvent is from about 0.3 to about 3.0 weight %, and the amount of the mercaptoundecanoic acid dissolved therein is from about 0.05 to about 0.5 weight %.

10. A surface acoustic wave gas sensor comprising:
a piezoelectric substrate;
an input transducer and an output transducer formed on the piezoelectric substrate; and
a sensitive film for detecting predetermined substances, the sensitive substance being formed between the input transducer and the output transducer,
wherein the sensitive film is formed by coating CMP and mercaptoundecanoic acid on the piezoelectric substrate, the CMP comprising cellulose nitrate, dibutyl phthalate, a mixture of benzene and ethanol, and ethyl acetate.

11. The surface acoustic wave gas sensor of claim 10, wherein the predetermined substances are at least one of acetone, benzene, dichloroethane, ethanol, and toluene.

12. The surface acoustic wave gas sensor of claim 10, wherein the CMP is comprised of:
from about 5 to about 25 weight % of cellulose nitrate;
from about 25 to about 50 weight % dibutyl phthalate;
from about 1 to about 10 weight % of a benzene-ethanol mixture; and
from about 40 to about 60 weight % of ethyl acetate.

13. The surface acoustic wave gas sensor of claim 12, wherein the amount of the CMP dissolved in the solvent is from about 0.3 to about 3.0 weight %, and the amount of the mercaptoundecanoic acid dissolved therein is from about 0.05 to about 0.5 weight %.

14. The surface acoustic wave gas sensor of claim 10, wherein the amount of the CMP dissolved in the solvent is from about 0.3 to about 3.0 weight %, and the amount of the mercaptoundecanoic acid dissolved therein is from about 0.05 to about 0.5 weight %.

15. A surface acoustic wave gas comprising:
a piezoelectric substrate;
an input transducer and an output transducer formed on the piezoelectric substrate; and
a sensitive film for detecting predetermined substances, the sensitive substance being formed between the input transducer and the output transducer,
wherein the sensitive film is formed by coating cellulose nitrate, dibutyl phthalate, a mixture of benzene and ethanol, ethyl acetate, and mercaptoundecanoic acid on the piezoelectric substrate.

16. The surface acoustic wave gas sensor of claim 15, wherein the predetermined substances are at least one of acetone, dichloroethane, ethanol, and toluene.

17. The surface acoustic wave gas sensor of claim 15, wherein a ratio of the cellulose nitrate dissolved in the acetone is from about 0.3 to about 3.0 weight %.

18. The sensitive substance of claim 1, wherein the solvent is acetone.

19. The sensitive substance of claim 4, wherein the solvent is acetone.

20. A method of using a sensitive substance which comprises using a sensitive substance in an acoustic wave gas sensor by dissolving the sensitive substance in a solvent so as to detect predetermined substances in the acoustic wave gas sensor, the sensitive substance comprising cellulose nitrate, dibutyl phthalate, a mixture of benzene and ethanol, ethyl acetate, and mercaptoundecanoic acid.

* * * * *